(12) United States Patent
Schumacher et al.

(10) Patent No.: US 10,926,013 B2
(45) Date of Patent: Feb. 23, 2021

(54) METHODS AND SYSTEMS FOR AN EXTERNAL DRIVE UNIT FOR AN IMPLANTABLE HEART ASSIST PUMP

(71) Applicant: ECP ENTWICKLUNGSGESELLSCHAFT MBH, Berlin (DE)

(72) Inventors: Jörg Schumacher, Teltow (DE); Gerd Spanier, Aachen (DE); Thorsten Siess, Aachen (DE); Maxim Daschewski, Berlin (DE); Jim-Po Wang, Danvers, MA (US)

(73) Assignee: ECP ENTWICKLUNGSGESELLSCHAFT MBH, Aachen (DE)

( * ) Notice: Subject to any disclaimer, the term of this patent is extended or adjusted under 35 U.S.C. 154(b) by 65 days.

(21) Appl. No.: 15/482,513

(22) Filed: Apr. 7, 2017

(65) Prior Publication Data
US 2018/0289877 A1    Oct. 11, 2018

(51) Int. Cl.
*A61M 1/12* (2006.01)
*A61M 1/10* (2006.01)
*A61M 25/02* (2006.01)

(52) U.S. Cl.
CPC .......... *A61M 1/127* (2013.01); *A61M 1/1034* (2014.02); *A61M 1/122* (2014.02);
(Continued)

(58) Field of Classification Search
CPC .... A61M 1/122; A61M 1/101; A61M 1/1086; A61M 1/1012; A61M 1/1001; A61M 1/1029; A61M 2202/0413; A61M 2205/04; A61M 2205/33; A61M 2205/3576; A61M 2205/36; A61B 5/0031; A61B 2018/00577; A61B 18/00; A61B 18/08; A61B 18/12;
(Continued)

(56) References Cited

U.S. PATENT DOCUMENTS 5,947,892 A  *  9/1999  Benkowski ............. A61M 1/10
                                                       415/900
2006/0247738 A1    11/2006  Schmeling et al.
(Continued)

FOREIGN PATENT DOCUMENTS

WO    1989005668 A2    6/1989

OTHER PUBLICATIONS

International Search Report PCT/EP2018/058942 dated Jun. 27, 2018 (4 pages).
EP Search Report EP17187359 dated Jan. 22, 2018 (3 pages).

*Primary Examiner* — Deborah L Malamud
(74) *Attorney, Agent, or Firm* — Botos Churchill IP Law LLP

(57) ABSTRACT

The application relates to an external drive unit (7) for an implantable heart assist pump. The proposed drive unit (7) comprises a motor (35) for driving the heart assist pump, wherein the motor (35) is connectable to the heart assist pump via a transcutaneous drive shaft (3). The drive unit (7) further comprises a heat spreader (19) comprising a contact surface configured to contact and/or directly contact and/or lie flat against a skin of a patient. The contact surface is connected or connectable with the motor (35) in a thermally-conductive manner to transfer heat generated by the motor (35) to tissue of the patient.

20 Claims, 7 Drawing Sheets

(52) U.S. Cl.
CPC ..... *A61M 25/02* (2013.01); *A61M 2025/0266* (2013.01); *A61M 2205/04* (2013.01); *A61M 2205/3666* (2013.01); *A61M 2205/8262* (2013.01)

(58) Field of Classification Search
CPC ....... B29L 2031/7496; B29L 2031/753; B29L 2031/7532; B29L 2031/7534; A61F 2/06; A61F 7/00
See application file for complete search history.

(56) References Cited

U.S. PATENT DOCUMENTS

| | | |
|---|---|---|
| 2007/0106274 A1 | 5/2007 | Ayre et al. |
| 2015/0073509 A1 | 3/2015 | Kallmyer et al. |
| 2016/0213827 A1 | 7/2016 | Tanner et al. |

\* cited by examiner

METHODS AND SYSTEMS FOR AN EXTERNAL DRIVE UNIT FOR AN IMPLANTABLE HEART ASSIST PUMP

BACKGROUND

The present application relates to the field of medical technology. The application relates to an external drive unit for an implantable heart assist pump and to a heart assist device comprising the drive unit and the implantable heart assist pump. Further, the present application relates to a method of operation of the heart assist device.

Heart assist devices for assisting a heart function of a patient are known from the state of the art. Such devices may comprise an implantable blood pump which may be inserted into a ventricle of the heart by minimally invasive means. Further, an external (or extracorporal) motor may be supplied to drive the blood pump. The motor may be connected with the blood pump via a transcutaneous and flexible drive shaft which may be rotatably mounted inside a transcutaneous catheter. The implantable components of the device may be inserted via a puncture site in a patient's groin. A related device is described, e.g., in U.S. Pat. No. 8,489,190 B2.

For such heart assist devices problems may arise relating to heat dissipated by the external motor. In some applications, the motor may be disposed close to the patient's body, in particular close to the patient's leg, while the blood pump is operated. If heat generated by the motor is not effectively removed the motor may overheat, which may cause malfunction of the motor. In addition, overheating of the motor may constitute a health risk to the patient when a hot housing of the motor contacts the skin of the patient, in particular when the patient is not able to notice the heat and to react appropriately, e.g., due to anesthetic medication. Safe amounts of heat absorption by a human skin have been studied in the context of heat generated by ultrasound and magnetic resonance imaging probes. For example, in "Human Skin Temperature Response to Absorbed Thermal Power" (SPIE Proceedings—The International Society for Optical Engineering 3037:129-134, March 1997) a method is described to determine safe levels of heat absorption.

To prevent the motor of the heart assist device from overheating, the housing of such a motor may be equipped with a multitude of cooling fins so that heat is effectively withdrawn from the motor and dissipated to the surrounding air. However, the amount of heat transferrable to the air may not be sufficient if the motor is operated in an enclosed environment, e.g., underneath a duvet while the patient rests or underneath surgical drapery during surgery. In addition, a surface of the housing with cooling fins may be difficult to clean.

SUMMARY

In view of the aforementioned state of the art, it is an objective of the present application to provide an improved external drive unit for an implantable heart assist pump and an improved heart assist device. Further, the present application relates to an improved method of operation of the heart assist device. In particular, it is an objective of the application to enable a safe and efficient operation of the heart assist device.

These objectives are achieved by an external drive unit with the features of independent claim 1 and by a method according to claim 16. Optional further features and further developments will become apparent from the dependent claims and the detailed description in conjunction with the accompanying drawings.

The proposed external (extracorporal) drive unit for an implantable heart assist pump comprises a motor for driving the heart assist pump, wherein the motor is connectable or connected to the heart assist pump via a transcutaneous drive shaft. The drive unit further comprises a heat spreader comprising a contact surface configured to contact and/or directly contact and/or lie flat against a skin of a patient. The contact surface is connected or connectable with the motor in a thermally-conductive manner to transfer heat generated by the motor to tissue of the patient.

The contact surface may be flat or curved. In typical embodiments, the contact surface is stepless. In a preferred embodiment the contact surface is flexible to maximize the contact to the tissue. The contact surface is provided for the transfer of heat from the motor to the tissue. The entire contact surface may come into contact with the skin while the drive unit is in use. The drive unit may further comprise a bottom surface formed by an entirety of all areas of the drive unit designed to come into contact the skin of the patient. The contact surface typically forms a part of the bottom surface. However, in some embodiments, the contact surface forms the entire bottom surface.

The application further relates to a heart assist device comprising the drive unit as described above or below and further comprising the implantable heart assist pump. The heart assist device may further comprise the transcutaneous drive shaft. The heart assist pump may be connected, for example unseparably connected, with the drive unit via the drive shaft. In another embodiment the drive unit maybe connected to the drive shaft via a coupling, for example via a magnetic clutch.

In addition, the application relates to a method of operation of the heart assist device. In this method, the drive unit drives the heart assist pump and the contact surface of the heat spreader contacts and/or directly contacts and/or lies flat against the skin of the patient such that heat generated by the motor is transferred to the tissue of the patient. In most embodiments, the contact surface of the heat spreader directly contacts the skin of the patient. However, in some cases another material may be arranged between the skin and the contact surface, e.g., a piece of clothing of the patient.

The motor typically comprises a housing, and the heat spreader may be attached to the housing of the motor. The heat spreader may be rigidly or movably connected with the housing of the motor. In some embodiments, the heat spreader is removably connected with the housing. For example, it may be convenient to implant the heart assist pump in the catheterization lab with the heat spreader disconnected. The motor housing may serve as a handle of the heart assist device in this situation. After the implantation procedure, the motor housing may be connected with motor so that heat generated by the motor may be efficiently transferred to tissue of the patient.

The drive unit may comprise a holding means configured to attach the drive unit to a thigh of the patient. When the heart assist device is use, in a typical application scenario at least the bottom surface of the drive unit comes into contact with the skin of the patient. The contact surface may then also come into contact with the skin. The proposed drive unit then allows for an efficient removal of heat from the motor during operation of the motor. Thereby, overheating of the motor may be prevented from occurring.

In typical embodiments, cooling fins are not needed. Hence, the proposed drive unit may be designed in a comparably compact manner, which improves an ease of attaching the drive unit and a comfort of wear of the drive unit. Further, the amount of heat removed from the motor is foreseeable and not strongly dependent on temperatures of ambient air or flow rates of ambient air. Therefore, a heat management of the drive unit may be controlled in a reliable manner. Also, because the cooling fins are not needed, the housing may have a partly or fully continuous and/or stepless surface. Hence, the drive unit may be easy to clean.

Therefore, the drive unit may be advantageously used in different application scenarios: First, during implantation of the heart assist device in a catheterization laboratory the motor may be placed above a sterile drapery, because the region underneath the drapery may be considered non-sterile. In this situation, convection of air around the motor is possible, which reduces the risk of overheating. Furthermore, unintended contact of the patient with the motor is unlikely, and a contact of the user (physician) with the motor typically occurs with gloves. The acceptable temperature of the motor is thus higher than in the second application scenario described below. Further, a risk of contamination of the drive unit is relatively high, because the user may touch the motor with contaminated, in particular bloodstained, gloves.

Second, during patient transport or at an intensive care unit it is especially important that the pump keeps its position inside the patient. In this situation, the motor, due to its weight, should be fixed reliably in relation to the puncture site. For this purpose, the motor is usually placed underneath a blanket or duvet. Thus, heat transfer from the motor by convection is not efficient, and a risk of overheating of the motor during operation has to be considered. Further, direct contact of the patient with the pump is likely in this scenario. Hence, the efficient heat transfer from the motor to tissue of the patient as ensured by the proposed drive unit is highly beneficial. Further, as after a longer time of use the motor may need to be cleaned, the surface geometry that may be obtained with the proposed drive unit is beneficial as compared with designs of heat sinks known from the art, e.g., comprising cooling fins.

In some embodiments, a surface area of the contact surface is at least 25 cm$^2$, preferably at least 50 cm$^2$ or at least 100 cm$^2$. Typically, the surface area is smaller than 400 cm$^2$. A sufficiently large surface area is necessary to enable an efficient transfer of heat from the motor to tissue of the patient. In addition, a sufficiently large surface area is important to prevent a local overheating of the tissue and damage to the tissue from occurring. An amount of heat transferred to the tissue of the patient is typically at most 80 mW per cm$^2$, preferably at most 60 mW per cm$^2$ or at most 40 mW per cm$^2$, of a surface area of the contact surface. Further, the surface area constitutes an important factor when designing the heat management of the drive unit and enables the motor to be operated at a desired temperature. In most embodiments, during operation of the drive unit a ratio of the surface area of the contact surface and the heat dissipated by the motor is at least 13 cm$^2$/W, preferably 25 cm$^2$/W and especially preferred 50 cm$^2$/W to avoid local overheating of the tissue.

The heat spreader may be flexible at least in areas. Thereby, the contact surface may adapt to a contoured surface of the skin. For example, the contact surface can adapt to a shape of the thigh when the drive unit is attached to the thigh of the patient. Hereby, a comfort of wear of the drive unit may be improved and a thermal contact between the heat spreader and the skin of the patient may be ensured. The heat spreader may be flexible in all areas of the heat spreader.

The heat transferred to the tissue usually does not serve a therapeutic purpose. To enable an efficient transfer of heat from the motor to the tissue of the patient, the heat exchanger may comprise at least a section of a material with a relatively high thermal conductivity. This region may fully extend over the contact surface. The thermal conductivity in this region may be at least 1 W/(m·K), preferably at least 10 W/(m·K), at least 50 W/(m·K), or at least 100 W/(m·K). In a preferred embodiment, the thermal conductivity of the heat spreader is higher in a direction parallel to the contact surface of the heat spreader than perpendicular to the contact surface to ensure that the heat energy is widely spread over the surface and to avoid hot spots.

Since for the safe and efficient transfer of heat from the motor to tissue of the patient a distribution of the heat across the surface area is of primary importance, the weight of the drive unit and the amount of material necessary may be reduced by designing the heat spreader such that it is of a flat shape. Hence, the heat spreader may comprise a thickness of less than 2 cm, in particular less than 1 cm or less than 0.5 cm. For example, the heat spreader may be a foil.

The heat spreader may comprise a thermally conductive layer. The thermally conductive layer may enable a rapid and efficient transfer of heat across the area of the contact surface so that hot spots on the skin are avoided. The heat spreader may further comprise a carrier layer. The carrier layer may have a lower thermal conductivity than the thermally conductive layer. The carrier layer may contain an elastomer and/or plastic. In this manner, the thermally conductive layer, in particular a relatively thin and/or flexible layer, may enable a sufficient transfer of the heat while the carrier layer may supply a sufficient mechanical stability of the heat spreader. The thermally conductive layer may contain a metal, in particular copper, aluminium and/or pyrolytic carbon. In some embodiments, the heat spreader may comprise more than one thermally conductive layer.

In addition, the heat spreader may comprise a biocompatible coating. For example, the contact surface of the heat spreader may comprise a biocompatible coating. The coating may form a part of a bottom surface of the heat spreader or fully form the bottom surface of the heat spreader. The coating may cover and/or enclose the thermally conductive layer. In particular, the coating may be provided if the heat spreader or its thermally conductive layer comprises harmful substances, which may be dissolvable in sweat. The coating may then prevent the harmful substances from reaching the skin of the patient. For example, the biocompatible coating may contain parylene, polyurethane, silicone, PEEK, or a biocompatible, for example an implantable metal. The biocompatible coating may have a thickness of less than 2 mm, preferably less than 0.5 mm or less than 0.1 mm. The biocompatible coating may be identical with the carrier material building a biocompatible carrier.

Further, the motor and/or a motor housing may be elongated. The motor may be elongated such that a direction of elongation of the motor and/or of the motor housing coincides with an axial direction of the thigh when the drive unit is attached to the thigh of the patient. The holding means is typically connected with the housing of the motor. The holding means of the drive unit may comprise a strap and/or a hook-and-loop fastening means. The holding means may further comprise an adhesive. An adhesive attachment of the drive unit to the thigh allows for a particularly reliable fixation of the drive unit with respect to the puncture site. In particular, when the drive unit is attached to the thigh of the patient, the adhesive fixation may form an effective holding means that prevents the drive unit from sliding down a tapered portion of the thigh towards the knee. For example, mechanical stress exerted on the puncture site may be reduced by the suggested holding means. In some embodiments, the heat spreader comprises an adhesive surface for attaching the heat spreader to the skin. For example, the heat spreader may be formed by an adhesive patch. The adhesive surface may form a part of the contact surface and/or the entire contact surface. The adhesive may be a biocompatible adhesive as for example well known from adhesive wound closure patches.

Further, the drive unit may comprise a means of fixation to prevent shifting of the drive unit to different positions on the skin of the patient. For example, the means of fixation may comprise rubberized areas. The bottom surface of the drive unit may further comprise nubs.

The heat spreader may comprise openings or recesses, in particular through holes or grooves, to allow for an evaporation of sweat from the skin. The openings or recesses may be at least partially disposed adjacent to the contact surface. In typical embodiments, the heat spreader comprises at least three, at least five or at least eight openings or recesses. During operation of the motor heat transferred to tissue of the patient may result in an enhanced perspiration of the patient. Therefore, the openings or recesses may significantly improve a comfort of wear of the drive unit. To achieve an efficient transfer of vapour to the ambient air, a smallest or uniform diameter of the openings or recesses is typically at least 1 mm or at least 5 mm. A largest or the uniform diameter of the openings or recesses is typically at the most 20 mm or 80 mm.

In some embodiments, the openings are elongated. A ratio of the largest diameter to the smallest diameter may be at least 1.2 or at least 2. In this way, the sweat (in the form of vapour) may be efficiently transferred from the body to the ambient air, while a sufficient mechanical stability and an efficient two-dimensional heat conduction in the heat spreader is ensured. For example, the openings may be elongated such that the openings exhibit a larger diameter in a circumferential direction of the thigh and a smaller diameter in the axial direction of the thigh when the drive unit is attached to the thigh of the patient. If the motor is elongated in the axial direction, the elongation of the holes may allow for the heat to be efficiently transferred in the circumferential direction, while the vapour is efficiently removed from the skin.

In some embodiments, the heat spreader comprises pores to allow for vapourized sweat to be transferred from the skin to ambient air. The heat spreader may comprise a membrane with the pores. The pores may have diameter of at least 0.02 µm and/or at most 0.3 µm.

The heat spreader may comprise a sweat absorbent material, in particular a textile or cotton. The sweat absorbent material may form a part of the bottom surface of the heat spreader. The sweat absorbent material may absorb sweat from the skin of the patient and hence improve the comfort of wear of the drive unit.

In some embodiments, the heat spreader comprises a heat pipe. The heat pipe may be flat. For example, the heat pipe may be a heat diffusor. Typically, a bottom surface of the heat pipe comes into contact with the skin of the patient. In other embodiments, a heat pipe may be arranged between and connected with the motor and the heat spreader. A top surface of the heat pipe may be in thermal contact with the motor. The heat pipe may enable an efficient transfer of heat from the motor to the tissue or to the contact surface.

The motor may comprise a stator and rotor. The rotor typically comprises a magnet, in particular a permanent magnet. The stator may comprise a multitude of windings. The stator typically surrounds the rotor, such that a magnetic gap is formed between the magnet of the rotor and the windings of the stator. The rotor may be rotatably mounted. The motor may further be connectable or connected to the drive shaft. In some embodiments, a fluid gap is formed between the rotor and the stator. The fluid gap may be in fluid connection with a purge opening for injecting a purge medium into the fluid gap. The purge medium may be a solution, e.g., a glucose solution or saline solution. Typically, the heart assist device comprises a catheter surrounding the drive shaft. The purge medium may be injected into the fluid gap and into a lumen of the catheter, for example a space between the catheter and the drive shaft. The fluid gap of the motor is usually in fluid connection with the lumen of the catheter or with the space between the catheter and the drive shaft.

When unpurged motors are used a seal may be necessary to separate the motor from the space between the catheter and the drive shaft to avoid air from entering into the space and eventually into the patient. The use of a purged motor has the advantage that a complex seal separating the motor from the space between the catheter and the drive shaft may not be necessary. Hence, the motor may be easier to fabricate and friction losses of the motor may be reduced so that the motor may be operated in a more efficient manner. However, friction losses in the purge medium may be expected to lead to a reduced efficiency of the purged motor as compared with an un-purged motor. Surprisingly, a disadvantageously low efficiency of the motor may be circumvented by any one of the features described below and by a combination of these features.

A width of the fluid gap may be at least 0.1 mm, preferably at least 0.2 mm, and/or at most 1 mm, preferably at most 0.5 or at most 0.3 mm. It has to be considered that a minimal size of the magnetic gap is limited by a size of the fluid gap. Typically, the rotor and/or the stator comprise a sleeve or a coating which may delimit the fluid gap. The delimiting surfaces of the fluid gap may be smooth and/or stepless and may avoid undercut surfaces to ensure a reliable venting process. Hereby, the rotor magnet and/or the stator windings may be protected from a corrosive effect of the purge medium. As a consequence, the magnetic gap is typically larger than the fluid gap. Although the magnetic losses are expected to increase with increasing width of the fluid (and magnetic) gap, it was surprisingly found that the relatively large width of the fluid gap leads to an overall improvement of the efficiency of the motor. This improvement is related to a reduction of the friction losses in the purge medium.

As explained above, the proposed drive unit allows for a precise control of the heat management of motor in various application scenarios. In particular, the temperature of the purge medium in the fluid gap may be precisely controllable. In typical embodiments, the temperature of the purge medium in the fluid gap is at least 50° C., preferably at least 60° C., in a steady state of operation. Further, the temperature of the purge medium in the fluid gap is at most 100° C., preferably at most 90° C., in a steady state of operation. By controlling the temperature of the purge medium accordingly, the viscosity of the purge medium may be decreased while the temperature of the purge medium may be kept safe for the patient and the purge medium is prevented from boiling. Therefore, the motor may be operated in a particularly efficient manner by controlling the temperature of the purge medium such that the friction losses in the fluid are low.

To precisely control the temperature of the purge fluid, the heat transfer between the fluid gap and the skin of the patient has to be analysed and coordinated. For example, a heat transfer from the fluid gap to the heat spreader may be influenced by a material of the housing of the motor. The housing may contain or be made of a plastic material, e.g., PEEK or ABS. The plastic material is particularly suited to enable operation of the motor in the desired temperature range. In some embodiments, the housing of the motor is shaped such that it may be used as a handle of the drive unit.

According to the following aspects, the drive unit may not comprise a heat spreader as described above or below and/or the drive unit comprises a heat spreader which may not be brought in contact with the skin of the patient. A means of heat removal from the motor may, for example, be formed by the heat spreader as discussed above or below, by cooling fins attached to a housing of the motor, or by a heat pipe connected with the motor in a thermally conductive manner. Further embodiments become apparent from the combinations of the aspects with one another and/or with the description above or below.

Described herein, inter alia, are methods and systems for an external drive unit for an implantable heart assist pump.

In one aspect, a method of operation of a heart assist device comprising an external drive unit and an implantable heart assist pump, wherein the drive unit comprises a motor for driving the heart assist pump, and wherein the motor is connected to the heart assist pump via a transcutaneous drive shaft, wherein the motor comprises a stator and a rotatably mounted rotor connectable to the drive shaft, wherein a fluid gap is formed between the rotor and the stator, wherein the fluid gap is in fluid connection with a purge opening for injecting a purge medium into the fluid gap, and wherein the heart assist device comprises a catheter surrounding the drive shaft, wherein a purge medium is injected into the fluid gap and into a space between the catheter and the drive shaft.

In some implementations, a temperature of the purge medium in the fluid gap is at least 50° C., preferably at least 60° C., in a steady state of operation.

In some implementations a temperature of the purge medium in the fluid gap is at most 100° C., preferably at most 90° C., in a steady state of operation.

In some implementations, the purge medium is a glucose solution or saline solution.

In another aspect, an external drive unit for an implantable heart assist pump comprises a motor for driving the heart assist pump, wherein the motor is connectable or connected to the heart assist pump via a transcutaneous drive shaft, wherein the drive unit comprises a heat pipe connected with the motor in a thermally conductive manner.

In some implementations, the drive unit comprises a motor housing and the heat pipe is connected with the housing in a thermally conductive manner.

In another aspect, a heart assist system comprising the drive unit further comprises a console or a controller unit with a heat sink, wherein a portion of the heat pipe is connected with the heat sink in a thermally conductive manner to remove heat from the motor.

BRIEF DESCRIPTION OF FIGURES

The foregoing and other objects and advantages will be apparent upon consideration of the following detailed description, taken in conjunction with the accompanying drawings, in which like reference characters refer to like parts throughout, and in which exemplary embodiments will be described.

DETAILED DESCRIPTION

Figure 1:
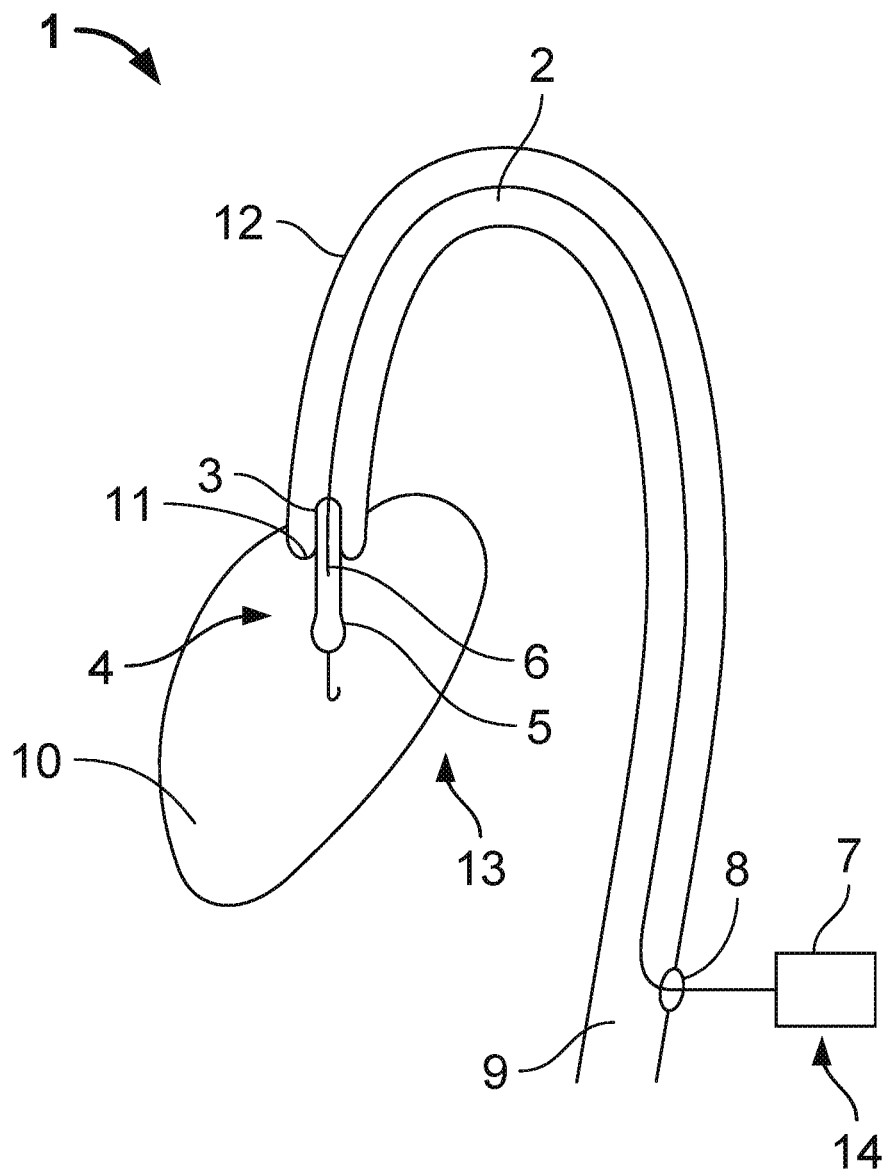
FIG. 1 is a schematic representation of a heart assist device with an implanted heart assist pump and an extracorporal drive unit.

A schematic representation of a heart assist device 1 is depicted in FIG. 1. The heart assist device 1 comprises a catheter 2. A flexible drive shaft 3 is guided inside the catheter 2. Distal ends of the catheter 2 and the drive shaft 3 are connected with a pump head of a heart assist pump 4. The heart assist pump 4 comprises a housing 5 and a propeller 6. The propeller 6 is connected with a distal and of the drive shaft 3. A proximal end of the drive shaft 3 is connected with an extracorporal drive unit 7 comprising a motor. The drive unit 7 is configured to drive a rotary motion of the propeller for moving blood of a patient.

The heart assist pump 4 as well as the catheter 2 and the drive shaft 3 are inserted into the femoral artery of the patient via a puncture site 8 located in the groin of the patient. The depicted arrangement illustrates the use of the heart assist device 1 to assist the left-ventricular function of the heart, wherein the heart assist pump 4 is partly arranged inside the left ventricle 10 of the patient in an area of the aortic valve 11. When the heart assist device 11 is operated, the drive shaft 3 is driven by the motor of the drive unit 7 and the heart assist device 11 conveys blood from the left ventricle 10 into the aorta 12, i.e., from a distal end 13 of the heart assist device 1 in a direction toward a proximal end 14. In other embodiments, the heart assist device 1 may be configured to convey blood in a direction from the proximal end 14 of the heart assist device 1 toward the distal end 13. Such an arrangement may be particularly suited for assisting a right-ventricular function of the heart.

Figure 2:
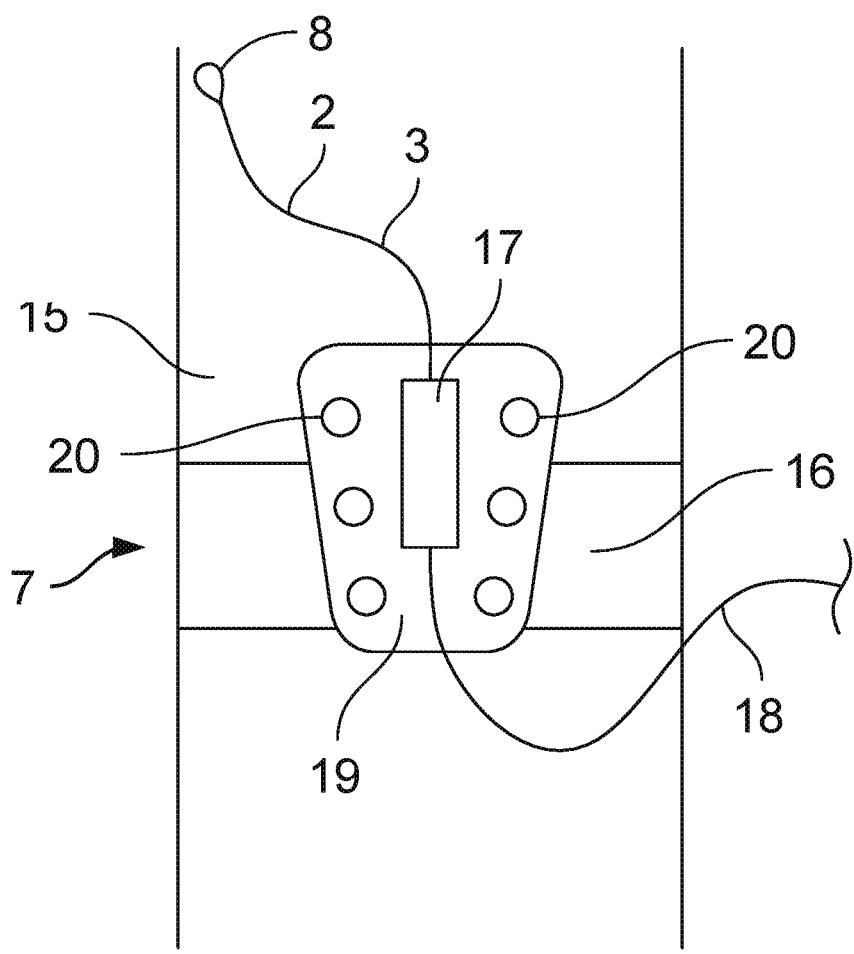
FIG. 2 is a schematic representation of the drive unit.

The drive unit 7 may be attached to a thigh 15 of the patient, as depicted schematically in FIG. 2. Reoccurring features in FIG. 2 and in the following figures are denoted using the same reference numerals. In the depicted embodiment, the drive unit 7 is held in place with respect to the puncture site 8 by a strap 16, e.g., an elastic strap. In most embodiments, a length of the strap is between 45 and 60 cm. Other means of fixation are possible, however, as discussed below. The motor is arranged inside a motor housing 17, e.g., formed by an injection moulded ABS part. A surface of the motor housing 17 is smooth and stepless in most embodiments so that the housing 17 is easy to clean and may serve as a handle of the heart assist device 1. The catheter 2 is rigidly connected with a proximal end of the motor housing 17 in a fluid-tight manner. Further, a supply line 18 is schematically shown in the figure. The supply line 18 is connected with a proximal end of the motor housing 17 and contains an electrical power supply line for the motor and a fluid supply line for a purge medium. In other embodiments, the fluid supply line and the power supply line are each guided inside one of multiple separate supply lines.

The drive unit 7 further comprises a heat spreader 19. The heat spreader 19 is rigidly connected with the motor housing 17 such that heat generated by the motor during operation is transferred to the heat spreader 19. The heat spreader 19 may be thin and have a thickness of 4 mm or less. For example, the heat spreader 19 may be formed by a patch as discussed below or by a flat, two-dimensional heat pipe. A bottom surface of the heat spreader 19 lies flat against and is in direct contact with the skin of the patient in a contact surface so that heat may be transferred from the heat spreader 19 to tissue of the patient. During operation of the motor a temperature of the outer surface of the housing 17 may exceed 43° C. before fixation of the heat spreader 19 to the thigh 15. However, the heat conductivity of the heat spreader 19 ensures that the heat is evenly spread over a sufficient area and transferred into the thigh 15 so that the temperature at the surface of the housing 17 decreases rapidly under a temperature of 42° C., which defines a critical temperature for damaging the tissue.

The heat spreader 19 comprises regions with a thermal conductivity of more than 100 W/(m·K) to spread the heat laterally so that the heat is efficiently transferred to the entire contact surface. A surface area of the contact surface may be as large as 200 cm$^2$ in some embodiments. The heat spreader 19 further comprises openings (through holes), two of which are denoted using the reference numerals 20 and 20'. The openings 20, 20' allow for a transfer of vaporized sweat to ambient air and hence increase a comfort of wear.

Figure 3:
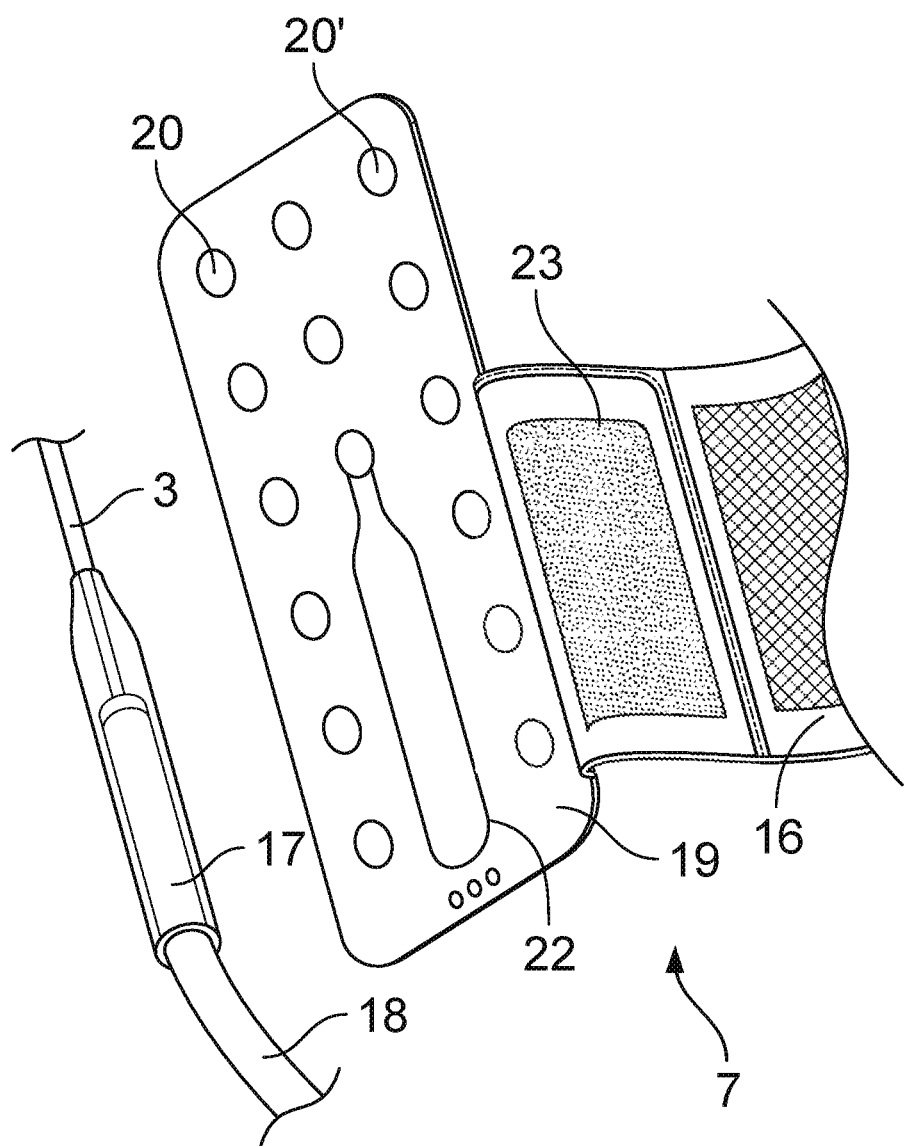
FIG. 3 is another schematic representation of the drive unit.

A perspective view of the drive unit 7 is shown in FIG. 3. In the depicted embodiment, the heat spreader 19 has a recess 22 for receiving the housing 17 of the motor. The strap 16 comprises a hook and loop fastening mechanism with a looped surface 23 for engaging a corresponding hooked surface disposed at an end portion of the strap and not depicted in the figure. When the heart assist device 1 is in use, the pump housing 17 is received in the recess 22, and the strap 16 is circumferentially wrapped around the thigh such that the motor housing 17 is covered by a portion of the strap 16 and the drive unit 7 is held in place.

Figure 4:
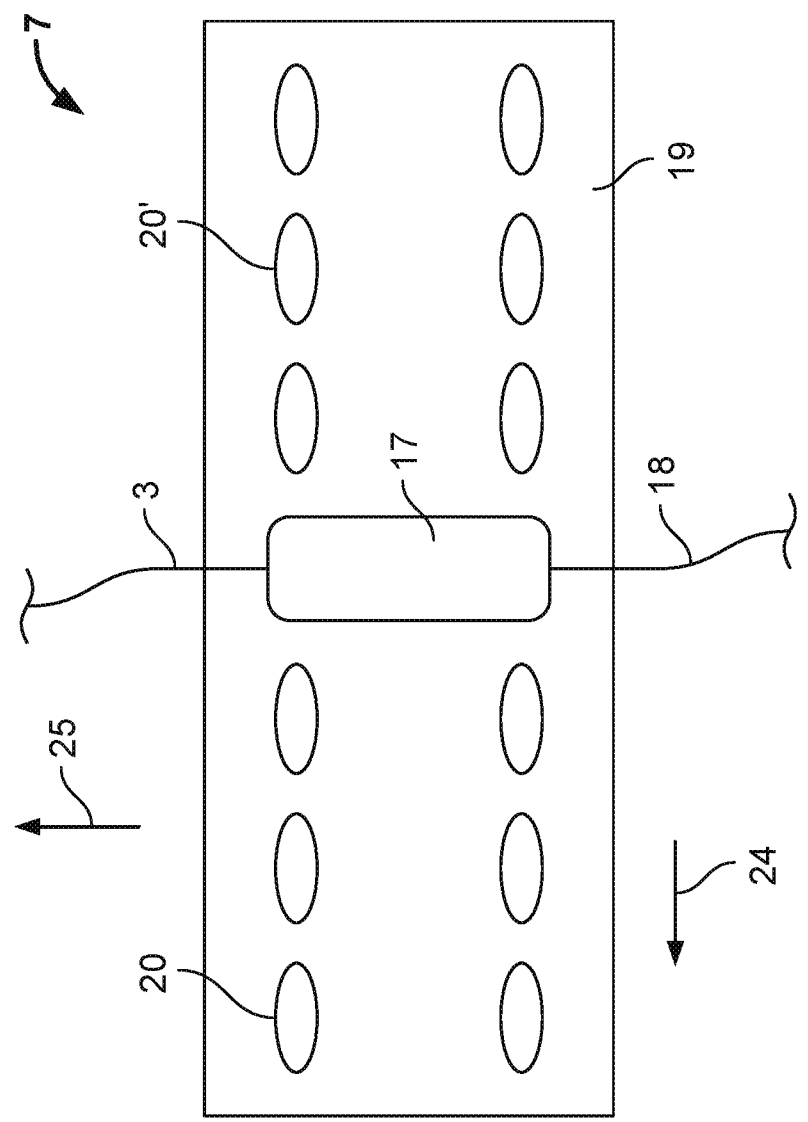
FIG. 4 is another schematic representation of the drive unit.

The openings 20, 20' of the heat spreader 19 may be elongated, as schematically depicted in FIG. 4. In this case, the openings 20, 20' exhibit a larger diameter in a circumferential direction 24 with respect to the thigh 15 to enable an efficient heat transport of the heat spreader 19 in this direction 24. The motor housing 17 is elongated in a perpendicular direction 25 corresponding to an axial direction 25 of the thigh 15.

Figure 5:
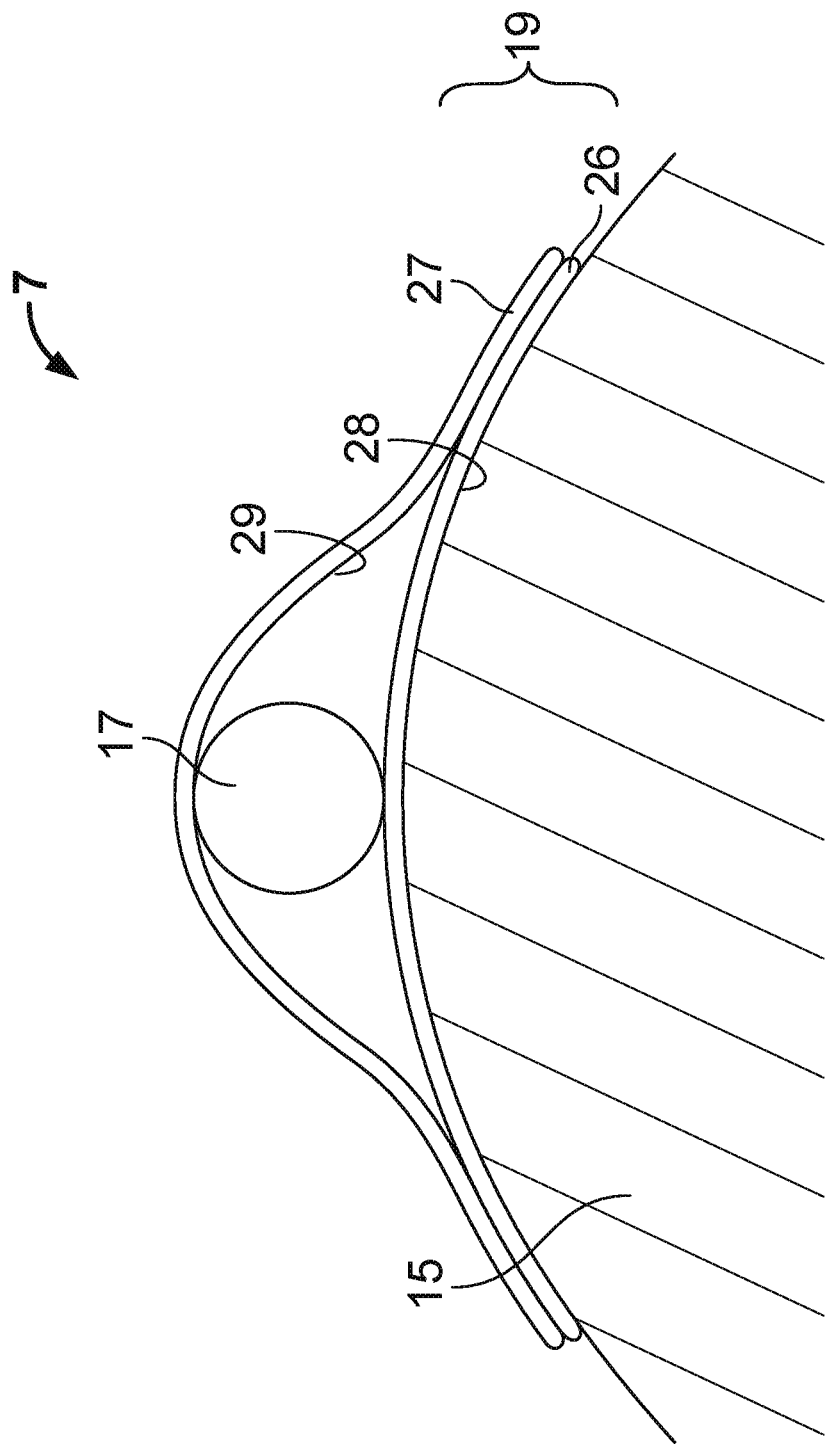
FIG. 5 is a schematic cross-sectional view of a heat spreader and a motor housing.

The heat spreader 19 may be curved and/or flexible to adapt to a shape of the thigh 15. For example, the heat spreader 19 may comprise a foil or a patch. FIG. 5 depicts an exemplary cross section through a heat spreader 19 formed by a first patch 26 and a second patch 27 and the motor housing 17. The patches 26, 27 are each bendable and each comprise adhesive bottom surfaces 28, 29 facing the thigh 15. The patches 26, 27 enclose the motor housing 17 in the depicted embodiment to efficiently draw heat from the motor. In the depicted embodiment the adhesive surfaces of the heat spreader 19 form a holding means to hold the drive unit 7 in place with respect to the puncture site 8. Therefore, another holding means, such as the strap 16 described above, may not be necessary, but may still be supplied in some embodiments.

Figure 6:
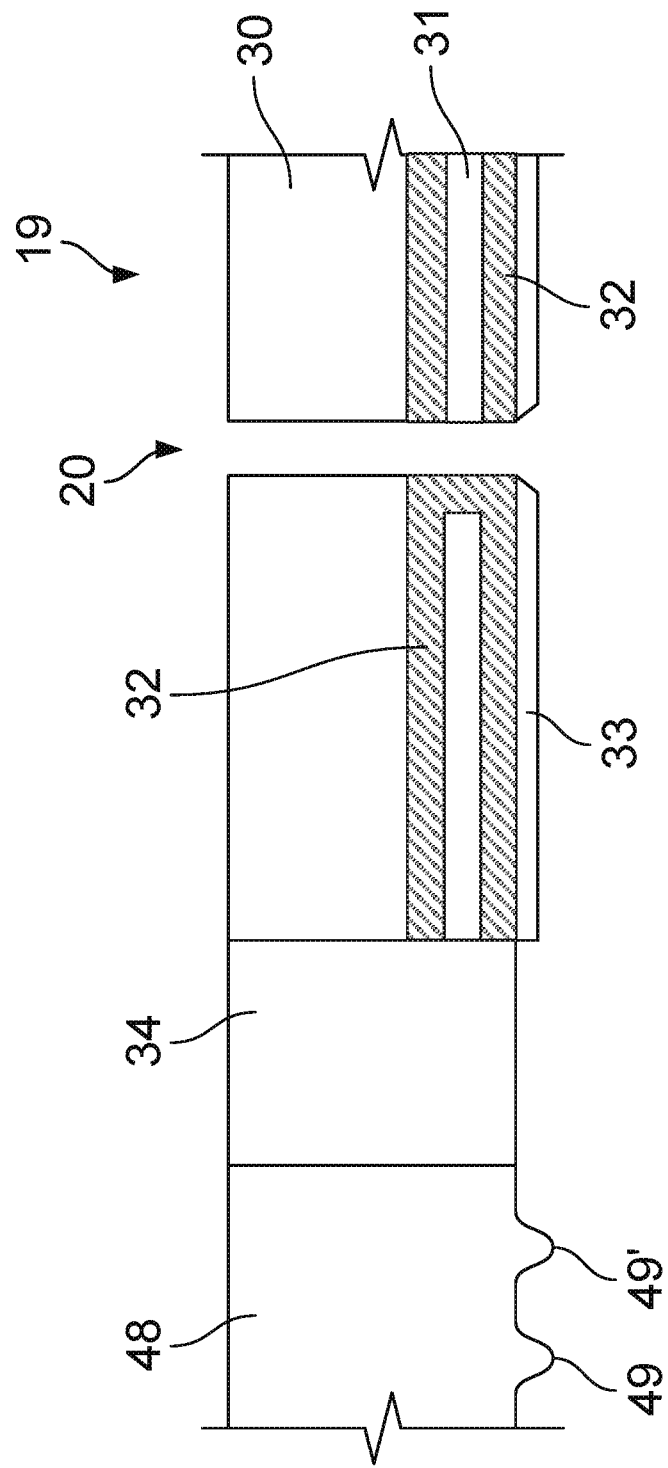
FIG. 6 is a schematic cross-sectional view of the heat spreader.

An exemplary cross section through the heat spreader 19 is shown in FIG. 6. The heat spreader 19 may be a multi-layered structure. The heat spreader 19 comprises carrier layer 30 that forms the top layer of the heat spreader 19. The carrier layer 30 may be formed by an elastomeric and/or plastic material. For an efficient heat transfer across the area of the contact surface, i.e., in a horizontal direction in the figure, the heat spreader 19 further comprises a thin thermally conductive layer 31, which may be formed by a thin layer of a material with a high thermal conductivity, e.g., copper, aluminium or pyrolytic carbon. The thermally conductive layer 31 is enclosed on either side by an inert and biocompatible coating 32 made of parylene, polyurethane, silicone, PEEK, or a biocompatible, for example an implantable metal. The biocompatible coating 32 further covers the thermally conductive layer 31 on inner walls of an opening 20 of the heat spreader 19. A stepless bottom surface of the heat spreader is formed by an adhesive layer 33, e.g., containing glue, to stick the heat spreader 19 to the skin of the patient.

Further, a sweat absorbent portion 34 of the heat spreader 19 or of the drive unit 7 is schematically depicted in FIG. 6. The sweat absorbent portion may, e.g., be made of textile and/or cotton. In addition, the heat spreader 19 or the drive unit 7 comprises a rubberized area 48 with rubber nubs 49, 49' to prevent the heat spreader 19 from sliding relative to the puncture site 8. The sweat absorbent portions 34 and the rubberized areas 48 may be distributed evenly across the bottom surface of the heat spreader 19.

Figure 7:
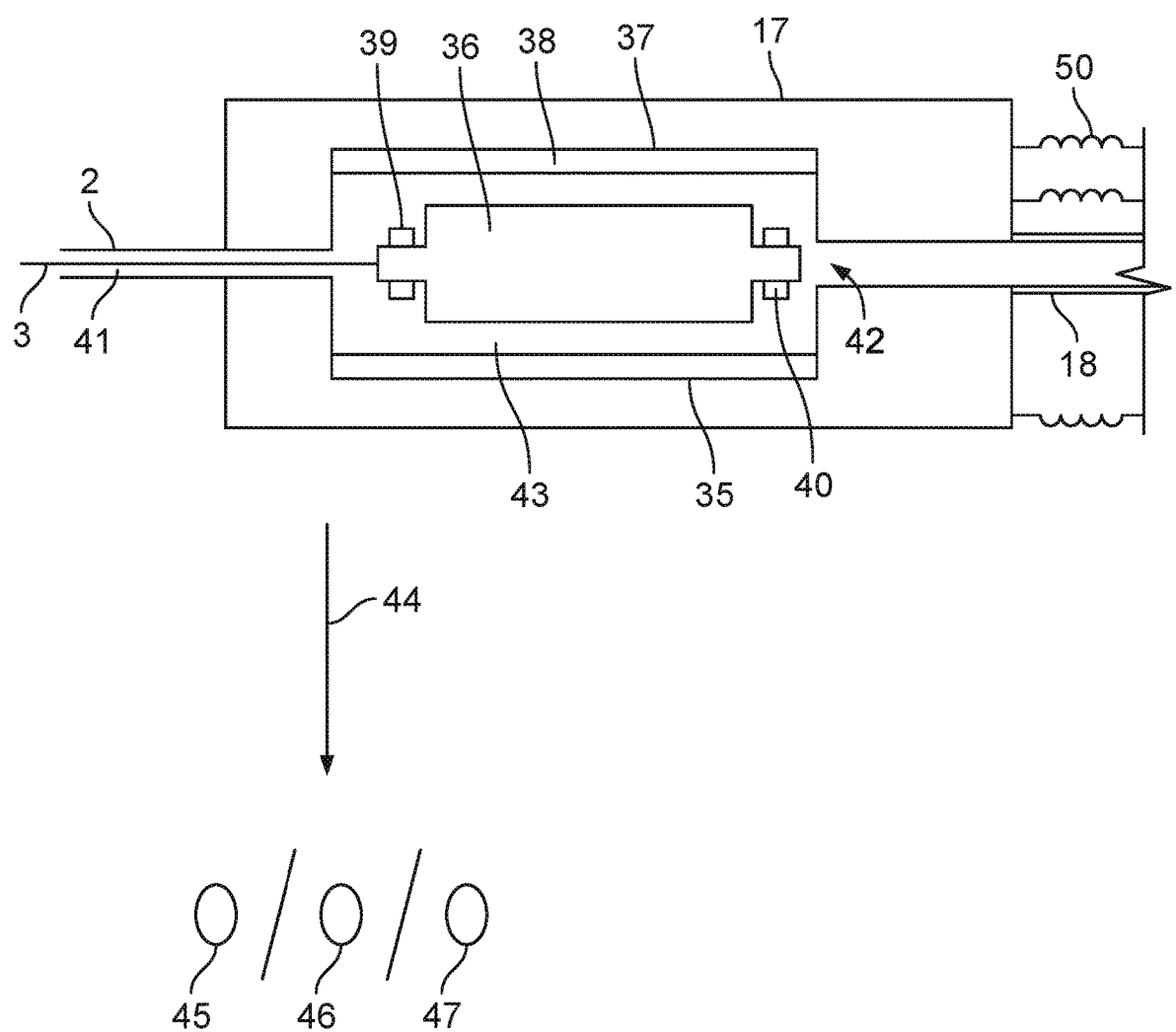
FIG. 7 is a schematic cross sectional view of the motor housing and a motor.

A schematic view of the motor 35 is shown in FIG. 7. The motor 35 is arranged inside the motor housing 17 and comprises a rotor 36 with a permanent magnet and a stator 37 with windings 38. The rotor 36 is rotatably mounted using a first bearing 39 and a second bearing 40 and may be rotated upon current flow through the windings of the stator 37. The rotor 36 is rigidly connected with the drive shaft 3 to drive the propeller 6.

The catheter 2 is rigidly connected with the motor housing 17, and a space 41 is formed between the catheter 2 and the drive shaft 3. This space 41 is in fluid connection with a fluid gap 43 formed between the rotor 36 and the stator 37, with a purge opening 42, and with the supply line 18. A width of the fluid gap 43 in a radial direction may be between 0.2 and 0.3 mm. When the heart assist device 1 is operated, a purge medium, e.g., a glucose solution, is supplied via the supply line 18 and flows through the fluid gap 43 and through the space 41 between the catheter 2 and the drive shaft 3 (and eventually into the patient at a proximal end of the heart assist device 1).

During operation of the motor 35 a power dissipation of, e.g., 2 W may cause the motor to heat up. The heat is removed from the motor 35 as schematically indicated by the arrow with the reference numeral 44 to keep a temperature of the glucose solution inside the fluid gap 43 constant at 75° C. in a steady state of operation. To remove the heat, the heat may, for example, be transferred to tissue 45 of the patient using the heat spreader 19 as discussed above, to ambient air 46, e.g., using cooling fins on the housing 17, or to a heat sink 47 of a console or a controller unit, e.g., via an elongated heat pipe connected to the housing 17. Combinations of these heat removal mechanisms are possible.

Further, inductors 50 may be supplied to reduce the eddy-current losses when the motor 35 is not driven in full block commutation. These inductors 50 can also be located inside the motor housing 17, but in a preferred embodiment the inductors 50 are located at the end of the motor cable 18 which is connected to the controller unit of the motor 35 (or in the controller unit itself) to avoid additional weight and heat sources at the motor 35 and at the patient's leg.

The foregoing is merely illustrative of the principles of the disclosure, and the methods and systems can be practiced other than the described implementations, which are represented for purposes of illustration and not of limitation. It is to be understood that the methods and systems disclosed herein, while shown for use in an implantable heart assist pump, may be applied to other cardiac assistance devices.

Variations and modifications will occur to those of skill in the art after reviewing this disclosure. The disclosed features may be implemented, in any combination and subcombination (including multiple dependent combinations and subcombinations), with one or more other features described herein. The various features described or illustrated above, including any components thereof, may be combined or integrated in other systems. Moreover, certain features may be omitted or not implemented.

Examples of changes, substitution, and alterations are ascertainable by one skilled in the art and could be made without departing from the scope of the information disclosed herein.

The invention claimed is:

1. A heart assist device comprising:
an external drive unit for an implantable heart assist pump;
the implantable heart assist pump; and
a transcutaneous drive shaft, wherein the external drive unit comprises a motor for driving the heart assist pump, wherein the motor is arranged within a motor housing, and the motor and the motor housing are located external to a patient, the motor configured to be connectable to the heart assist pump at least partially positioned within a heart of the patient via the transcutaneous drive shaft, wherein the motor comprises a stator and a rotatably mounted rotor connectable to the drive shaft, wherein a fluid gap is formed between the rotor and the stator, wherein the fluid gap is in fluid connection with a purge opening for injecting a purge medium into the fluid gap and wherein a catheter surrounds the transcutaneous drive shaft, wherein the purge medium is injected into the fluid gap and into a lumen of the catheter or into a space between the catheter and the drive shaft; and
a heat spreader comprising a contact surface configured to contact a skin of a patient, wherein the contact surface is connected or connectable with the motor via the motor housing in a thermally-conductive manner to transfer heat generated by the motor to tissue of the patient
wherein the implantable heart assist pump is connected with the external drive unit via the transcutaneous drive shaft, wherein the external drive unit drives the implantable heart assist pump, and wherein the contact surface of the heat spreader is configured to contact the skin of the patient such that heat generated by the motor is transferred to the tissue of the patient.

2. The external drive unit of claim 1, wherein a surface area of the contact surface is at least about 25 cm$^2$ or at least about 50 cm$^2$.

3. The external drive unit of claim 1, wherein the heat spreader is flexible at least in areas.

4. The external drive unit of claim 1, wherein the heat spreader is a foil or a patch.

5. The external drive unit of claim 1, wherein the heat spreader comprises a thermally conductive layer, and wherein the thermally conductive layer contains a metal and/or pyrolytic carbon.

6. The external drive unit of claim 5, wherein the metal comprises at least one of copper and aluminum.

7. The external drive unit of claim 1, wherein the heat spreader comprises a biocompatible coating.

8. The external drive unit of claim 1, wherein the heat spreader comprises an adhesive surface for attaching the heat spreader to the skin.

9. The external drive unit of claim 8, wherein the heat spreader comprises openings or recesses to allow for an evaporation of sweat from the skin.

10. The external drive unit of claim 9, wherein the openings are elongated.

11. The external drive unit of claim 1, wherein the heat spreader comprises a sweat absorbent material.

12. The external drive unit of claim 11, wherein the sweat absorbent material comprises one of cotton or a textile.

13. The external drive unit of claim 1, wherein a width of the fluid gap is at most 1 mm.

14. The external drive unit of claim 1, wherein a width of the fluid gap is at least 0.1 mm.

15. The external drive unit of claim 1, wherein the heat spreader comprises a heat pipe.

16. The external drive unit of claim 1, wherein an amount of heat transferred to the tissue of the patient is at most 80 mW per cm$^2$ of a surface area of the contact surface.

17. The external drive unit of claim 1, wherein a temperature of the purge medium in the fluid gap is at least 50° C., preferably at least 60° C., in a steady state of operation.

18. The external drive unit of claim 1, wherein a temperature of the purge medium in the fluid gap is at most 100° C., preferably at most 90° C., in a steady state of operation.

19. The external drive unit of claim 1, wherein the contact surface is mechanically connected or connectable with the motor via the motor housing.

20. The external drive unit of claim 1, wherein the contact surface is rigidly connected or connectable with the motor via the motor housing.

* * * * *